US010987121B2

(12) United States Patent
Gladstone

(10) Patent No.: US 10,987,121 B2
(45) Date of Patent: Apr. 27, 2021

(54) POWERED SURGICAL HANDPIECE HAVING A SURGICAL TOOL WITH AN RFID TAG

(71) Applicant: Medtronic Xomed, Inc., Jacksonville, FL (US)

(72) Inventor: Samuel Gladstone, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 381 days.

(21) Appl. No.: 16/160,022

(22) Filed: Oct. 15, 2018

(65) Prior Publication Data

US 2019/0046224 A1 Feb. 14, 2019

Related U.S. Application Data

(62) Division of application No. 14/227,765, filed on Mar. 27, 2014, now Pat. No. 10,130,382.

(51) Int. Cl.
*A61B 17/32* (2006.01)
*A61B 17/16* (2006.01)
*A61B 17/00* (2006.01)

(52) U.S. Cl.
CPC .. *A61B 17/320016* (2013.01); *A61B 17/1622* (2013.01); *A61B 17/1626* (2013.01); *A61B 2017/00199* (2013.01); *A61B 2017/00221* (2013.01)

(58) Field of Classification Search
CPC ........ A61B 17/320016; A61B 17/1626; A61B 17/1622; A61B 2017/00199; A61B 2017/00221
See application file for complete search history.

(56) References Cited

U.S. PATENT DOCUMENTS

| 4,675,648 A | 6/1987 | Roth et al. |
| 4,741,731 A | 5/1988 | Starck et al. |
| 5,207,697 A | 5/1993 | Carusillo et al. |
| 5,270,717 A * | 12/1993 | Schuermann ......... G01S 13/753 342/22 |

(Continued)

FOREIGN PATENT DOCUMENTS

| CN | 1831841 | 9/2006 |
| CN | 101067848 | 11/2007 |

(Continued)

OTHER PUBLICATIONS http://www.medtronic.com/for-healthcare-professionals/products-therapies/ear-nose-throat/powered-ent-instruments/powered-ent-instruments/integrated-power/index.htm, downloaded Mar. 27, 2014 (2 pages).

(Continued)

*Primary Examiner* — Phong Son H Dang
(74) *Attorney, Agent, or Firm* — Dicke, Billig & Czaja, PLLC

(57) ABSTRACT

A powered surgical handpiece includes a housing comprising a motor, and a surgical tool removably coupled to the housing and configured to be driven by the motor. The surgical tool includes a radio frequency identification (RFID) tag. The handpiece includes an antenna for wirelessly transmitting RF energy, and a coupler that is electrically isolated from the antenna and the RFID tag and that is configured to guide the transmitted RF energy to the RFID tag.

9 Claims, 6 Drawing Sheets

(56) References Cited

U.S. PATENT DOCUMENTS

| | | | |
|---|---|---|---|
| 5,383,874 A | 1/1995 | Jackson et al. |
| 5,400,267 A | 3/1995 | Denen et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,562,239 A | 10/1996 | Boiarski et al. |
| 5,651,780 A | 7/1997 | Jackson et al. |
| 5,693,042 A | 12/1997 | Boiarski et al. |
| 6,017,354 A | 1/2000 | Culp et al. |
| 6,068,627 A | 5/2000 | Orszulak et al. |
| 6,074,286 A | 6/2000 | Goble et al. |
| 6,074,386 A | 6/2000 | Goble et al. |
| 6,092,722 A | 7/2000 | Heinrichs et al. |
| 6,126,670 A | 10/2000 | Walker et al. |
| 6,237,604 B1 | 5/2001 | Burnside et al. |
| 6,283,961 B1 | 9/2001 | Underwood et al. |
| 6,308,089 B1 | 10/2001 | von der Ruhr et al. |
| 6,346,886 B1 | 2/2002 | De La Huerga |
| 6,387,092 B1 | 5/2002 | Burnside et al. |
| 6,402,743 B1 | 6/2002 | Orszulak et al. |
| 6,454,162 B1 | 9/2002 | Teller |
| 6,497,659 B1 | 12/2002 | Rafert |
| 6,500,169 B1 | 12/2002 | Deng |
| 6,578,579 B2 | 6/2003 | Burnside et al. |
| 6,611,793 B1 | 8/2003 | Burnside et al. |
| 6,626,355 B2 | 9/2003 | Sasse et al. |
| 6,635,067 B2 | 10/2003 | Norman |
| 6,651,669 B1 | 11/2003 | Burnside |
| 6,685,701 B2 | 2/2004 | Orszulak et al. |
| 6,733,495 B1 | 5/2004 | Bek et al. |
| 6,783,523 B2 | 8/2004 | Qin et al. |
| 6,792,390 B1 | 9/2004 | Burnside et al. |
| 6,825,754 B1 * | 11/2004 | Rolin | G06K 19/07756 |
| | | | 340/10.34 |
| 6,827,715 B2 | 12/2004 | Francischelli et al. |
| 6,843,789 B2 | 1/2005 | Goble |
| 6,861,954 B2 | 3/2005 | Levin |
| 6,893,435 B2 | 5/2005 | Goble |
| 6,899,538 B2 | 5/2005 | Matoba |
| 6,908,472 B2 | 6/2005 | Wiener et al. |
| 6,910,084 B2 | 6/2005 | Augustijn et al. |
| 6,977,495 B2 | 12/2005 | Donofrio |
| 7,044,949 B2 | 5/2006 | Orszulak et al. |
| 7,048,687 B1 | 5/2006 | Reuss et al. |
| 7,118,564 B2 | 10/2006 | Ritchie et al. |
| 7,158,030 B2 | 1/2007 | Chung |
| 7,169,144 B2 | 1/2007 | Hoey et al. |
| 7,176,030 B2 | 2/2007 | Faries, Jr. et al. |
| 7,177,533 B2 | 2/2007 | McFarlin et al. |
| 7,193,519 B2 | 3/2007 | Root et al. |
| 7,214,224 B2 | 5/2007 | Goble |
| 7,216,802 B1 | 5/2007 | De La Huerga |
| 7,217,269 B2 | 5/2007 | El-Galley et al. |
| 7,253,736 B2 * | 8/2007 | Tethrake | A61B 90/90 |
| | | | 340/572.7 |
| 7,256,696 B2 | 8/2007 | Levin |
| 7,258,546 B2 | 8/2007 | Beier et al. |
| 7,258,688 B1 | 8/2007 | Shah et al. |
| 7,289,139 B2 | 10/2007 | Amling et al. |
| 7,300,436 B2 | 11/2007 | Penny et al. |
| 7,420,468 B2 | 9/2008 | Fabian et al. |
| 7,443,296 B2 | 10/2008 | Mezhinsky et al. |
| 7,469,383 B2 | 12/2008 | Busch |
| 7,517,351 B2 | 4/2009 | Culp et al. |
| 7,551,077 B2 | 6/2009 | Raybuck et al. |
| 7,559,483 B2 | 7/2009 | Hickle et al. |
| 7,568,619 B2 | 8/2009 | Todd |
| 7,661,582 B2 | 2/2010 | Mollstam |
| 7,664,658 B2 | 2/2010 | Harrison et al. |
| 7,722,531 B1 | 5/2010 | Boche |
| 7,743,975 B2 | 6/2010 | Miller |
| 7,766,235 B2 | 8/2010 | Miller |
| 7,796,040 B2 | 9/2010 | Mezhinsky et al. |
| 7,821,402 B2 | 10/2010 | Yang et al. |
| 7,835,823 B2 | 11/2010 | Sillman et al. |
| 7,837,091 B2 | 11/2010 | Cook et al. |
| 7,837,694 B2 | 11/2010 | Tethrake et al. |
| 7,887,534 B2 | 2/2011 | Hamel et al. |
| 7,887,559 B2 * | 2/2011 | Deng | A61B 90/98 |
| | | | 606/170 |
| 7,934,648 B2 | 5/2011 | Charles et al. |
| 8,035,487 B2 | 10/2011 | Malackowski |
| 8,115,636 B2 | 2/2012 | Forster |
| 8,257,346 B2 | 9/2012 | Qin et al. |
| 8,500,769 B2 | 8/2013 | Deng |
| 8,535,342 B2 | 9/2013 | Malackowski et al. |
| 8,562,598 B2 | 10/2013 | Falkenstein et al. |
| 9,131,979 B2 | 9/2015 | Edwards et al. |
| 2003/0093103 A1 * | 5/2003 | Malackowski | A61B 17/1626 |
| | | | 606/170 |
| 2003/0139741 A1 | 7/2003 | Goble et al. |
| 2004/0054365 A1 | 3/2004 | Goble |
| 2004/0196693 A1 * | 10/2004 | Iwata | G11C 29/08 |
| | | | 365/158 |
| 2004/0267297 A1 | 12/2004 | Malackowski |
| 2005/0027311 A1 | 2/2005 | Wiener et al. |
| 2005/0080518 A1 * | 4/2005 | Wakefield, II | A61G 5/04 |
| | | | 701/1 |
| 2006/0206100 A1 | 9/2006 | Eskridge et al. |
| 2006/0208899 A1 * | 9/2006 | Suzuki | G06K 7/10178 |
| | | | 340/572.7 |
| 2007/0021766 A1 | 1/2007 | Belagali et al. |
| 2007/0026826 A1 * | 2/2007 | Wilson | G06K 19/0723 |
| | | | 455/130 |
| 2007/0029384 A1 * | 2/2007 | Atherton | G08B 13/2437 |
| | | | 235/435 |
| 2007/0119055 A1 * | 5/2007 | Walen | A61B 17/142 |
| | | | 30/144 |
| 2007/0213692 A1 | 9/2007 | Neubauer |
| 2007/0244825 A1 | 10/2007 | Semmer et al. |
| 2008/0129527 A1 | 6/2008 | Ohyama et al. |
| 2008/0165012 A1 * | 7/2008 | Choi | G06K 7/0008 |
| | | | 340/572.7 |
| 2008/0180221 A1 * | 7/2008 | Tuttle | G06K 19/0723 |
| | | | 340/10.2 |
| 2008/0211634 A1 * | 9/2008 | Hopkins | A61B 1/00029 |
| | | | 340/10.1 |
| 2008/0255413 A1 * | 10/2008 | Zemlok | A61B 17/072 |
| | | | 600/106 |
| 2008/0293008 A1 * | 11/2008 | Regere | A61C 1/0015 |
| | | | 433/119 |
| 2008/0297326 A1 | 12/2008 | Chakraborty et al. |
| 2009/0065565 A1 | 3/2009 | Cao |
| 2009/0090763 A1 | 4/2009 | Zemlok et al. |
| 2009/0261536 A1 | 10/2009 | Beale et al. |
| 2009/0264887 A1 | 10/2009 | Beale et al. |
| 2009/0264893 A1 | 10/2009 | Beale et al. |
| 2009/0264940 A1 | 10/2009 | Beale et al. |
| 2009/0292384 A1 * | 11/2009 | Hanawa | G06Q 10/0633 |
| | | | 700/104 |
| 2009/0299439 A1 | 12/2009 | Mire et al. |
| 2009/0315686 A1 | 12/2009 | Oberle |
| 2010/0010480 A1 * | 1/2010 | Mehta | A61B 18/14 |
| | | | 606/9 |
| 2010/0023008 A1 | 1/2010 | Heard et al. |
| 2010/0121320 A1 | 5/2010 | Hosier et al. |
| 2010/0121323 A1 * | 5/2010 | Pool | A61B 17/7016 |
| | | | 606/54 |
| 2010/0194536 A1 * | 8/2010 | Koo | G06K 19/0723 |
| | | | 340/10.1 |
| 2010/0262134 A1 | 10/2010 | Jensen et al. |
| 2010/0305563 A1 | 12/2010 | Varney |
| 2010/0321165 A1 * | 12/2010 | Lee | G06K 7/10891 |
| | | | 340/10.4 |
| 2011/0009699 A1 | 1/2011 | Slenker et al. |
| 2011/0017801 A1 * | 1/2011 | Zemlok | A61B 17/07207 |
| | | | 227/175.1 |
| 2011/0089248 A1 | 4/2011 | Deng et al. |
| 2011/0098698 A1 | 4/2011 | Bek et al. |
| 2011/0139851 A1 * | 6/2011 | McCuen | A61B 34/76 |
| | | | 227/175.1 |

(56) References Cited

U.S. PATENT DOCUMENTS

| | | | | |
|---|---|---|---|---|
| 2011/0152882 | A1* | 6/2011 | Wenderow | A61B 34/37 606/130 |
| 2011/0202023 | A1 | 8/2011 | Stanton et al. | |
| 2012/0238999 | A1* | 9/2012 | Estes | G16H 20/17 604/504 |
| 2012/0274253 | A1 | 11/2012 | Fair et al. | |
| 2012/0277546 | A1* | 11/2012 | Soykan | A61M 1/14 600/301 |
| 2013/0201006 | A1* | 8/2013 | Kummetz | G06K 7/10267 340/10.1 |
| 2013/0231656 | A1 | 9/2013 | Dunning | |
| 2013/0245704 | A1 | 9/2013 | Koltz et al. | |
| 2013/0256412 | A1* | 10/2013 | Yeh | G06K 7/10316 235/439 |
| 2014/0045441 | A1* | 2/2014 | Chen | H04B 1/525 455/78 |
| 2014/0276949 | A1* | 9/2014 | Staunton | F16D 15/00 606/130 |
| 2015/0032099 | A1 | 1/2015 | Larson et al. | |
| 2015/0196347 | A1* | 7/2015 | Yates | A61B 18/1445 606/48 |
| 2015/0335379 | A1 | 11/2015 | Edwards et al. | |

FOREIGN PATENT DOCUMENTS

| | | |
|---|---|---|
| CN | 102133122 | 7/2011 |
| DE | 4339049 | 5/1995 |
| EP | 2147651 | 1/2010 |
| JP | 2007-80202 | 3/2007 |
| JP | 2010158303 | 7/2010 |
| JP | 2011-62331 | 3/2011 |
| JP | 2013-255114 | 12/2013 |
| JP | 5467295 | 4/2014 |
| WO | 97/24073 | 7/1997 |
| WO | 2003/013372 | 2/2003 |
| WO | 2007002230 | 1/2007 |
| WO | 2007/030793 | 3/2007 |

OTHER PUBLICATIONS

International Search Report and Written Opinion of the International Searching Authority dated Jul. 22, 2015 regarding PCT/US2015/023003, 14 pages.

Design Ideas for Printed and Microstrip Antennas, YO3DAC-VA3IUL, Iulian Rosu, RF Technical Articles, http://www.qsl.net/va3iul/Antenna/Printed_and_Microstrip_Antennas/Design_Ideas_for_Printed_and_Microstrip_Antennas.htm, retrieved on Sep. 13, 2016 (11 pages).

Planar Spiral Monopole Antenna, YO3DAC-VA3IUL, Iulian Rosu, RF Technical Articles, http://www.qsl.net/va3iul/Antenna/Printed_and_Microstrip_Antennas/Planar_Spiral_Monopole_Antenna.gif, retrieved on Sep. 13, 2016 (1 page).

Spiral Antenna 433 MHz 916 MHz, YO3DAC-VA3IUL, Iulian Rosu, RF Technical Articles, http://www.qsl.net/va3iul/Antenna/Printed_and_Microstrip_Antennas/Spiral_Antenna_433MHz_916MHz.gif, retrieved on Sep. 13, 2016 (1 page).

Design of an Efficient Miniaturized UHF Planar Antenna, by K. Sarabandi and R. Azadegan, IEEE Transactions on Antennas and Propagation, vol. 51, No. 6, Jun. 2003 (7 pages).

\* cited by examiner

POWERED SURGICAL HANDPIECE HAVING A SURGICAL TOOL WITH AN RFID TAG

CROSS-REFERENCE TO RELATED APPLICATIONS

This application is a divisional of U.S. application Ser. No. 14/227,765, filed Mar. 27, 2014, entitled "Powered Surgical Handpiece having a Surgical Tool with an RFID Tag", the entire teachings of which are incorporated herein by reference.

BACKGROUND

Powered surgical handpieces are commonly used in many medical specialties to drive surgical tools. For example, powered surgical handpieces are used to drive surgical drills, blades or cutting instruments in performing various diverse cutting-type functions including drilling, tapping, resection, dissection, debridement, shaving, pulverizing, and shaping of anatomical tissue. In the areas of ENT/head/neck and spine surgery, the handpieces are typically configured for selective coupling to, and driving of, a variety of different rotary-type surgical instruments that are each designed to perform a specific procedure. During use, based upon the specific surgical procedure, the surgeon selects the appropriate surgical tool and mounts it to the powered handpiece. The powered handpiece is then operated to move one or more components of the tool (e.g., rotation, oscillation) required to perform the surgical procedure. Additional procedural steps can later be performed by mounting a differently-styled tool to the same powered handpiece. As a point of reference, the rotational speeds typically required by a powered surgical handpiece for spinal or other hard bone surgical procedures is in the range of about 10-250 rpm. ENT/head/neck procedures range from about 500 rpm for a laryngeal skimming operations to in excess of 60,000 rpm for high-speed drill operations.

In addition to motor improvements, such as use of brushless DC motors, overall systems have been developed for use with the powered rotary-type surgical handpiece and related surgical tools. A typical system, in addition to a powered handpiece and one or more rotary-type surgical tools or instruments, includes a control console and a cable that connects the handpiece to the console. The control console is configured to activate and/or control energization of the motor otherwise associated with the powered surgical handpiece. For example, a hand or foot switch can be provided as part of the system. Depending upon the surgeon's manipulation of the foot or hand switch, a corresponding signal is delivered to the control console that, in turn, energizes the handpiece to a corresponding speed.

The improved capabilities of powered surgical handpieces, as well as the vast number of surgical tools now available, have undoubtedly greatly increased the number of spine and ENT/head/neck procedures that a surgeon can perform utilizing a single surgical system. With these improvements, however, surgeons now desire even greater performance, operational capabilities, and safety with a single powered handpiece.

In light of the above, a need exists for a powered surgical handpiece providing enhanced performance capabilities in an ergonomically-sized housing.

SUMMARY

One embodiment is directed to a powered surgical handpiece that includes a housing comprising a motor, and a surgical tool removably coupled to the housing and configured to be driven by the motor. The surgical tool includes a radio frequency identification (RFID) tag. The handpiece includes an antenna for wirelessly transmitting RF energy, and a coupler that is electrically isolated from the antenna and the RFID tag, wherein the coupler is configured to guide the transmitted RF energy to the RFID tag.

Another embodiment is directed to a surgical system that includes a powered surgical handpiece comprising a motor, and a surgical tool removably connected to the surgical handpiece and configured to be driven by the motor. The surgical tool includes an ultra-high frequency (UHF) radio frequency identification (RFID) tag. The surgical system includes a controller connected to the surgical handpiece and programmed to interface with the surgical handpiece. The controller includes a data entry device and a display screen. The controller is configured to identify the surgical tool connected to the surgical handpiece based on data stored in the UHF RFID tag.

Yet another embodiment is directed to a method of identifying a surgical tool. The method includes providing a powered surgical handpiece comprising a motor, and a surgical tool removably connected to the surgical handpiece and configured to be driven by the motor. The method includes wirelessly transmitting RF energy from an antenna in the surgical handpiece, and guiding the transmitted RF energy to a radio frequency identification (RFID) tag in the surgical tool using an electrically isolated coupler in the surgical handpiece. The RF energy guided to the RFID tag enables the RFID tag to transmit data stored in the RFID tag. The method includes identifying the surgical tool connected to the surgical handpiece based on data transmitted from the RFID tag.

DETAILED DESCRIPTION

Figure 1:
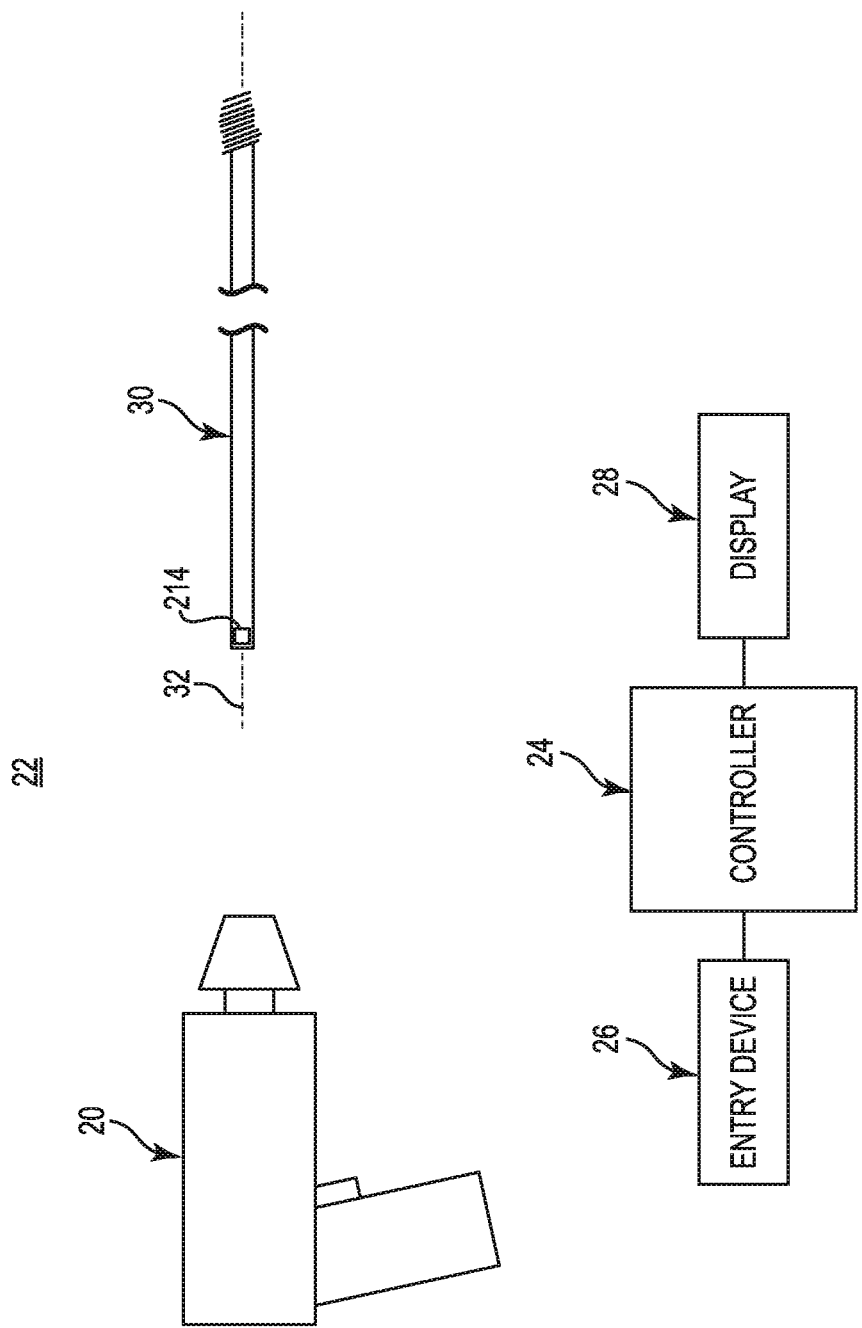
FIG. 1 is a block diagram illustrating a surgical system including a rotary-type powered surgical handpiece according to one embodiment.

FIG. 1 is a block diagram illustrating a surgical system including a rotary-type powered surgical handpiece 20 according to one embodiment. In some embodiments, the handpiece 20 is provided and/or is operated as part of a system 22 that further includes a controller 24. Where provided, the controller 24 has a microprocessor and can include (or be electronically connected to) one or more components such as a data entry device 26 and a display screen 28. Regardless, and in general terms, the handpiece 20 includes a housing comprising a motor and is configured to selectively receive a surgical instrument or tool 30. In one embodiment, the surgical tool 30 is a disposable blade or burr. Once connected to the controller 24, the system 22, and in particular the handpiece 20, is operated by a user to rotationally drive the instrument 30 in performing a desired surgical procedure, with the controller 24 providing control over the handpiece 20 based on information automatically signaled from the handpiece 20. Various features can be incorporated into the handpiece 20 and/or into the system 22 as a whole, including motor control and feedback, stimulation energy or nerve integrity monitoring, quick connect/disconnect between the handpiece 20 and the tool 30, safety over-rides based on user finger sensing, mode-function-direction control at the handpiece 20, high torque operation at very low and high speeds, etc.

System 22 according to one embodiment is configured to perform surgical tool recognition (or blade recognition) to automatically identify the surgical tool 30 currently attached to handpiece 20 using wireless ultra-high frequency (UHF) based radio frequency identification (RFID) technology. An RFID tag 214 is included in the surgical tool 30. System 22 performs an identification or recognition of surgical tool 30 without prior storing of specific product information in either the controller 24 or the handpiece 20. The RFID tag 214 according to one embodiment is permanently affixed into a hub of the surgical tool 30 with the top and bottom surfaces of the tag 214 being parallel to a longitudinal axis or attachment axis 32 of the surgical tool 30 (i.e., the RFID tag 214 is affixed in a non-axial orientation).

Figure 2:
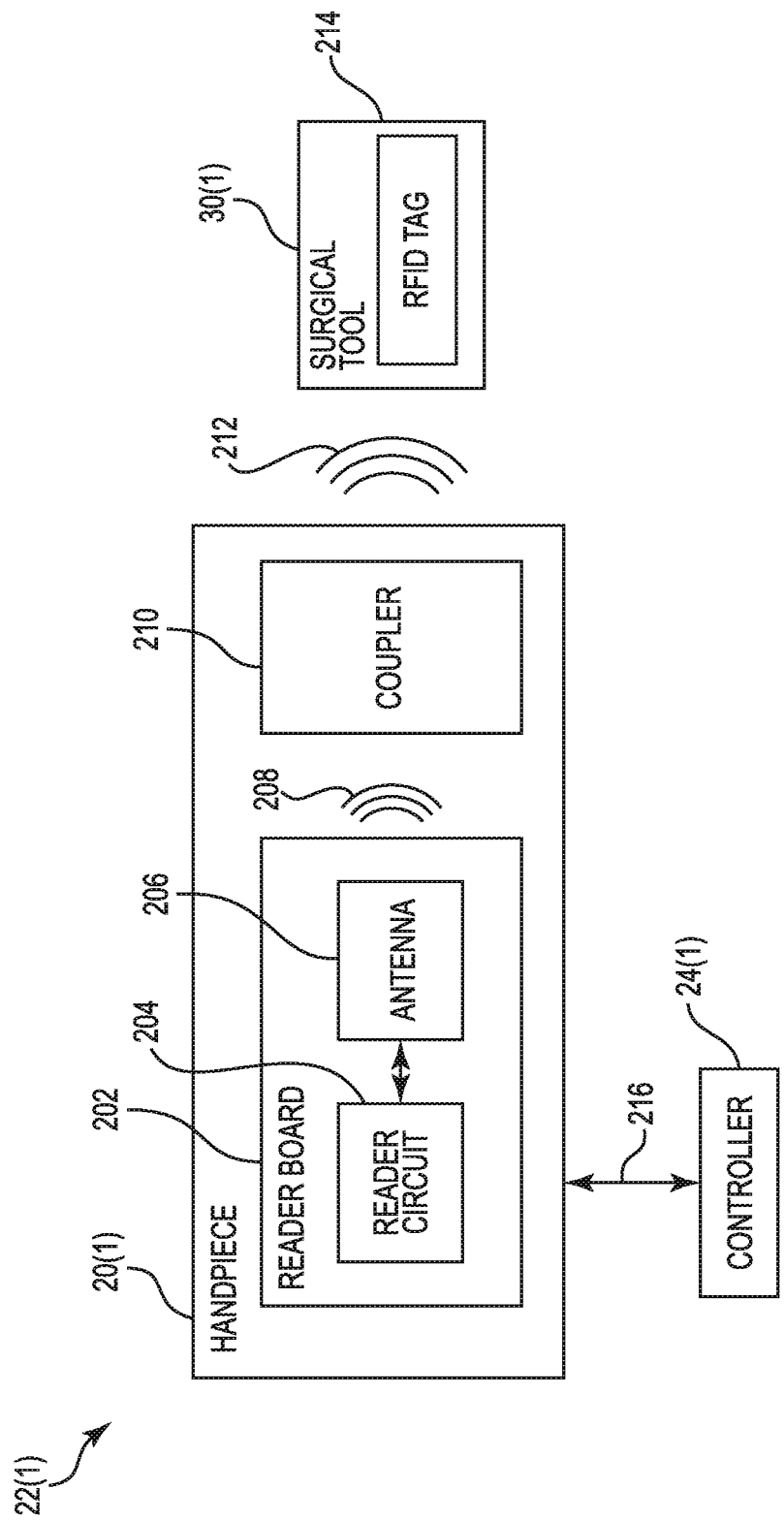
FIG. 2 is a block diagram illustrating components of the surgical system shown in FIG. 1 according to one embodiment.

FIG. 2 is a block diagram illustrating components of the surgical system 22 shown in FIG. 1 according to one embodiment. The embodiment of the surgical system 22 shown in FIG. 2 is identified by reference number 22(1). Surgical system 22(1) includes handpiece 20(1), surgical tool 30(1), and controller 24(1). Handpiece 20(1) includes RFID reader board 202 and coupler 210. Reader board 202 includes RFID reader circuit 204 and RFID antenna 206. Surgical tool 30(1) includes RFID tag 214.

The controller 24(1) transmits commands to the reader circuit 204 through a communication link 216, which is a cable with a serial digital line in one embodiment. The RFID reader circuit 204 drives the antenna 206, which transmits RF energy 208 to the coupler 210. In one embodiment, the RFID reader circuit 204 comprises an integrated circuit chip that is RFID Generation 2 Compatible (ISO 18000-6C Standard). The RFID reader circuit 204 includes an internal power amplifier, and a 20 dBm transmit power. The RFID reader circuit 204 includes reading and writing capabilities to read data from RFID tag 214 and write data to RFID tag 214.

The antenna 206 is a small ceramic element that is integrated into the reader board 202 in one embodiment. In one embodiment, antenna 206 is a ceramic antenna from Johanson Technology (part number 0920AT50A080), with a footprint of 11 mm×5.1 mm×1.5 mm (length×width×thickness). In another embodiment, antenna 206 comprises a printed circuit board (PCB) microstrip. The RFID reader board 202 with integrated antenna 206 is positioned proximate to the coupler 210 in the handpiece 20(1).

Coupler 210 is a passive rigid metal structure (single-piece or single construction) that is encapsulated in plastic and is electrically isolated, and is installed in the handpiece 20(1) at the time of manufacturing of the handpiece 20(1). The coupler 210 functions as a waveguide between antenna 206 and RFID tag 214, and channels RF energy from antenna 206 to RFID tag 214. The RFID tag 214 is a passive element located in a base portion of the surgical tool 30(1). The coupler 210 is not electrically connected to either the antenna 206 or the RFID tag 214, but rather couples RF energy to these elements by being proximate to these elements. Because of the lack of direct connections, the coupler 210 may also be referred to as a "floating coupler." As shown in FIG. 2, RF energy 208 is transmitted from antenna 206 and received by coupler 210. The RF energy 208 passes through coupler 210 and is emitted from coupler 210 as RF energy 212, which is received by RFID tag 214. The RF energy 212 powers the passive RFID tag 214 to allow the RFID tag 214 to wirelessly transmit stored information back to the reader circuit 204 through the coupler 210 and the antenna 206.

In one embodiment, RFID tag 214 comprises an Impinj RFID chip that is RFID Generation 2 Compatible (ISO 18000-6C Standard). RFID tag 214 according to one embodiment stores from 128 bits to 8 k bits, and contains a unique 64 bit serial number stored in ROM. RFID tag 214 has a footprint of 1.6 mm×1.6 mm×0.35 mm (length×width×thickness), and an operational frequency of 860 MHz to 960 MHz.

Figure 3:
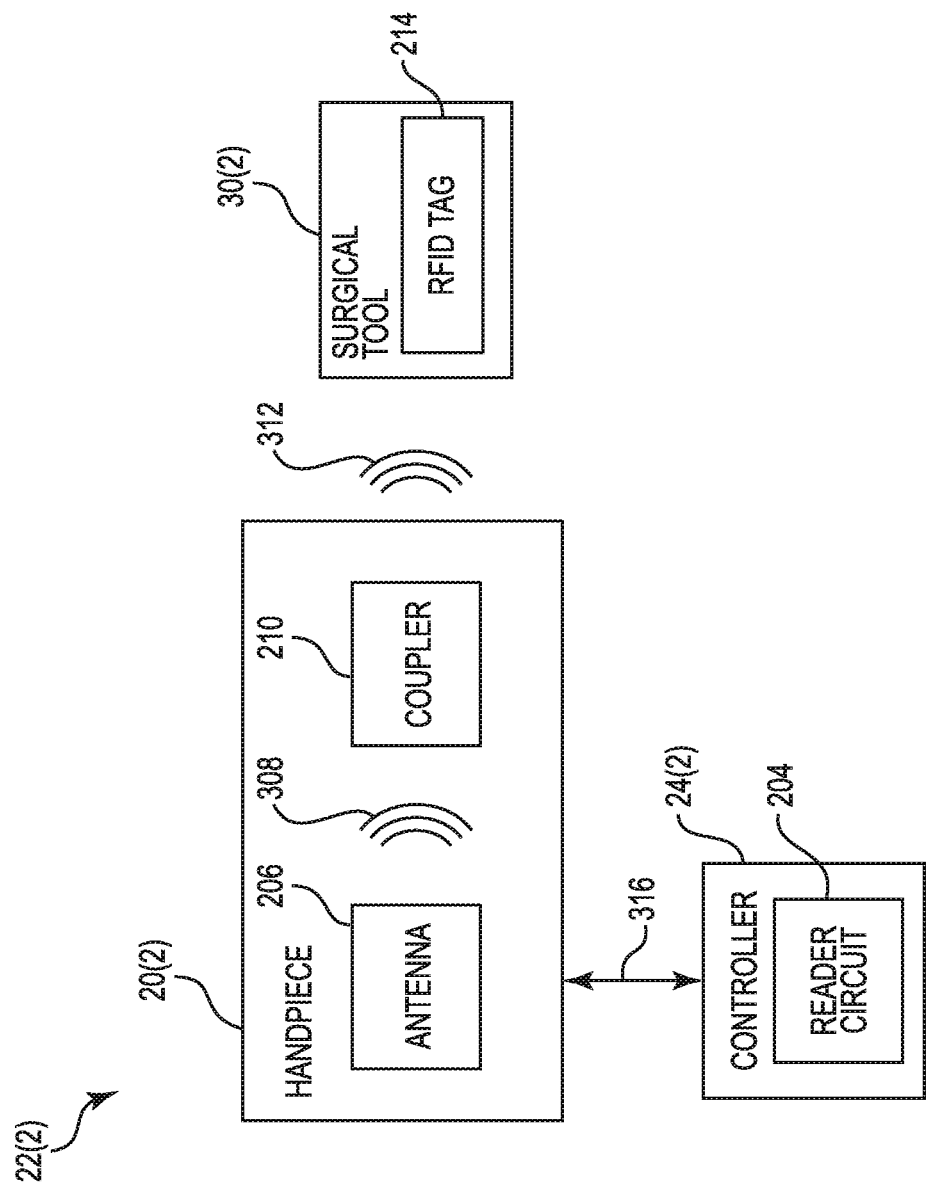
FIG. 3 is a block diagram illustrating components of the surgical system shown in FIG. 1 according to another embodiment.

FIG. 3 is a block diagram illustrating components of the surgical system 22 shown in FIG. 1 according to another embodiment. The embodiment of the surgical system 22 shown in FIG. 3 is identified by reference number 22(2). Surgical system 22(2) includes handpiece 20(2), surgical tool 30(2), and controller 24(2). Handpiece 20(2) includes RFID antenna 206 and coupler 210. Surgical tool 30(2) includes RFID tag 214. Controller 24(2) includes RFID reader circuit 204.

The RFID reader circuit 204 is installed in the controller 24(2). Communication link 316 includes a UHF coaxial cable or a twisted pair, such as those contained in a Cat 7A/8 cable, to deliver RF signals to the antenna 206 in the handpiece 20(2). Inside the handpiece 20(2), antenna 206 is positioned proximate to the coupler 210 to pass RF energy 308 through the coupler 210 to the RFID tag 214, as indicated by RF energy 312. The elements of surgical system 22(2) operate in substantially the same manner as surgical system 22(1), which was described above with reference to FIG. 2.

Figure 4:
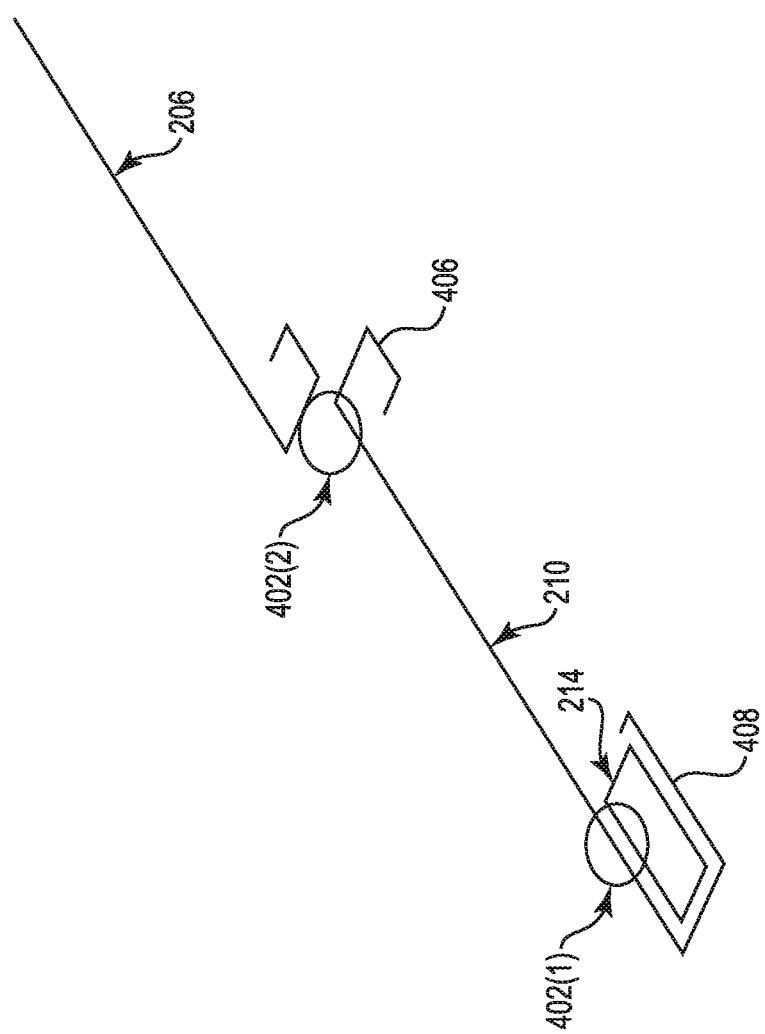
FIG. 4 is a diagram illustrating the near field coupling between a coupler and an antenna, and between the coupler and an RFID tag, according to one embodiment.

FIG. 4 is a diagram illustrating the near field coupling between the coupler 210 and the antenna 206, and between the coupler 210 and the RFID tag 214, according to one embodiment. The coupler 210 includes a proximal end 406 positioned adjacent to the antenna 206 but not in contact with the antenna 206, and a distal end 408 positioned adjacent to the RFID tag 214 but not in contact with the RFID tag 214. The close proximity of the distal end 408 of the coupler 210 to the RFID tag 214 provides near field coupling 402(1) between these elements, and the close proximity of the proximal end 406 of the coupler 210 to the antenna 206 provides near field coupling 402(2) between these elements.

Figure 5:
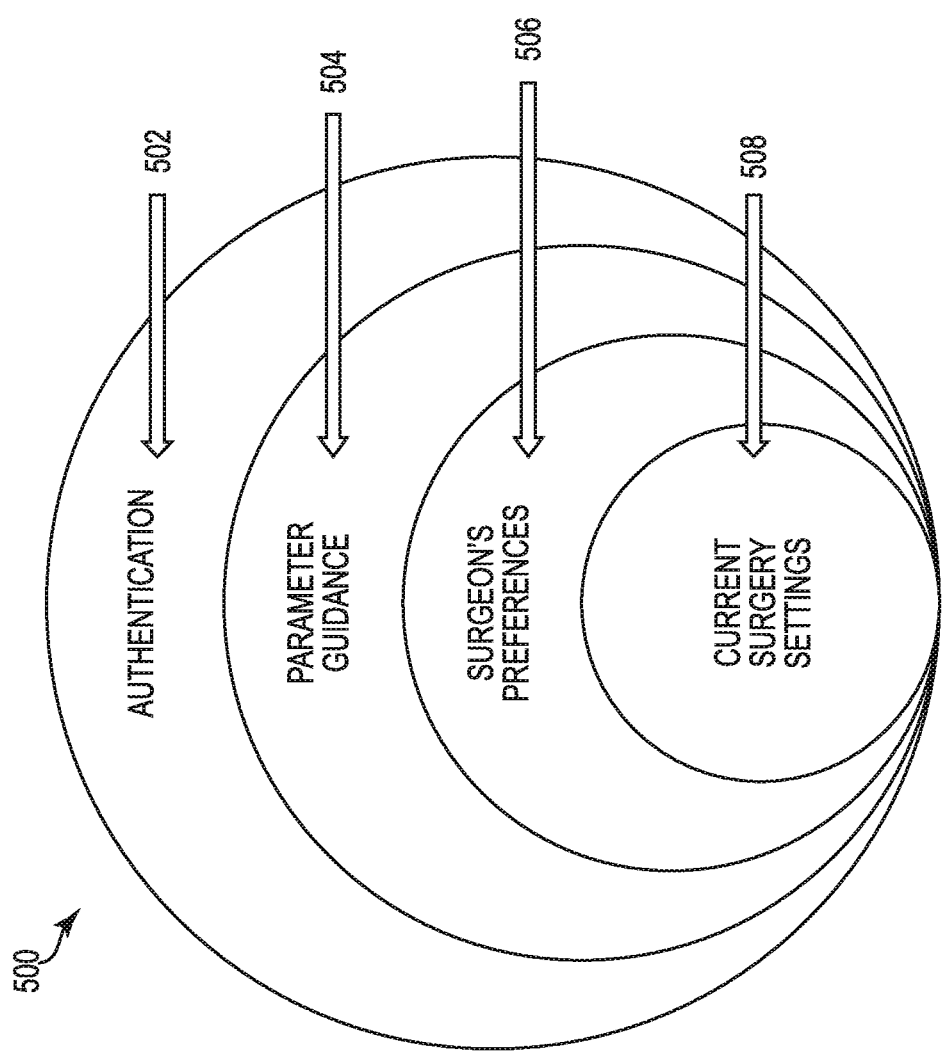
FIG. 5 is a diagram illustrating data stored in an RFID tag according to one embodiment.

FIG. 5 is a diagram illustrating data 500 stored in the RFID tag 214 according to one embodiment. As shown in FIG. 5, data 500 includes authentication data 502, parameter guidance data 504, surgeon preference data 506, and current surgery settings data 508. Authentication data 502 according to one embodiment includes a unique serial number, an authentication code, and written data, and may be used to prevent improper use or reuse of the surgical tool 30 containing the RFID tag 214. Parameter guidance data 504 according to one embodiment includes parameter data such as the type and/or model number of the surgical tool 30 containing the RFID tag 214 (e.g., a 4 mm Tricut Blade); operational limits such as minimum and maximum rotational speeds (e.g., in rotations per minute or RPM); optimal or recommended operational parameters, which may be used as default settings, such as optimum or recommended rotational speed and irrigation flow. Surgeon preference data 506 according to one embodiment includes the surgeon's preferred rotational speed (e.g., 2500 RPM), and the surgeon's preferred irrigation flow (e.g., 40% irrigation flow). Current surgery settings data 508 according to one embodiment includes the current or last used settings for surgical tool 30 containing the RFID tag 214, including rotational speed, irrigation flow, and length of time used. Data 500 may be encoded as scalar numbers (e.g., RPM speed), floating point numbers (e.g., irrigation flow percentage), or boolean values (e.g., true/false, yes/no).

Before operating the handpiece 20, information from the RFID tag 214, such as for example, parameters for safe operation of the surgical tool 30 (e.g., blade or burr) are read from the RFID tag 214 by the reader circuit 204. This information is sent to the controller 24 for setting operational guidance and limits. Data may also be written to the RFID tag 214 during use of the handpiece 20, including updating the surgeon preference data 506 and current surgery settings data 508. This data may also be stored in controller 24 to facilitate a quick change and re-use of different surgical tools 30. After the surgical tool 30 has been removed from the handpiece 20, the serial number of the RFID tag 214 for that tool 30 can be retained in a table by the controller 24 for later use. If a previously used surgical tool 30 for that surgery is reinserted into the handpiece 20, the serial number can be read and matched with the table in the controller 24. This allows the prior settings of the controller 24 for that surgical tool 30 to be remembered and recalled back to the operating settings. This potentially can reduce time for changing surgical tools 30 during a procedure.

One embodiment provides for the storage of default preferences for each surgeon. The surgeon's preferences for operating parameters are stored in the controller 24 prior to the surgery. Stored default parameters are, for example, the default rotational speed or irrigation settings that are referenced to a particular model number of a surgical tool 30. The stored defaults are not limited to being referenced to a single model number but can be associated with a family of products as well.

One embodiment is directed to a powered surgical handpiece that includes a housing comprising a motor, and a surgical tool removably coupled to the housing and configured to be driven by the motor. The surgical tool includes a radio frequency identification (RFID) tag. The handpiece includes an antenna for wirelessly transmitting RF energy, and a coupler that is electrically isolated from the antenna and the RFID tag and that is configured to guide the transmitted RF energy to the RFID tag.

In one form of this embodiment, the RF energy comprises ultra-high frequency (UHF) RF signals. The coupler according to one embodiment is a passive metal structure encapsulated in plastic. In one embodiment, the powered surgical handpiece includes an RFID reader circuit in the housing that is configured to drive the antenna and read data from and write data to the RFID tag. The RFID tag stores authentication data including a unique serial number; parameter guidance data including operational limits and default operational parameters; a surgeon's preferred operational parameters; and last used operational parameters from a last time that the surgical tool was used. In one embodiment, the handpiece automatically uses the last used operational parameters again when the surgical tool is removed and later re-used in the handpiece.

Another embodiment is directed to a surgical system that includes a powered surgical handpiece comprising a motor, and a surgical tool removably connected to the surgical handpiece and configured to be driven by the motor. The surgical tool includes an ultra-high frequency (UHF) radio frequency identification (RFID) tag. The surgical system includes a controller connected to the surgical handpiece and programmed to interface with the surgical handpiece. The controller includes a data entry device and a display screen. The controller is configured to identify the surgical tool connected to the surgical handpiece based on data stored in the UHF RFID tag.

In one form of this embodiment, the surgical handpiece includes an antenna for wirelessly transmitting RF energy, and a coupler that is electrically isolated from the antenna and the UHF RFID tag and that is configured to guide the transmitted RF energy to the UHF RFID tag. The coupler is a passive metal structure encapsulated in plastic. In one embodiment, the surgical handpiece includes an RFID reader circuit that is configured to drive the antenna and read data from and write data to the UHF RFID tag. In another embodiment, the controller includes an RFID reader circuit that is configured to drive the antenna and read data from and write data to the UHF RFID tag. In one form of this embodiment, the controller is coupled to the surgical handpiece via a cable that includes a twisted pair configured to deliver UHF RF energy to the antenna. The UHF RFID tag stores authentication data including a unique serial number; parameter guidance data including operational limits and default operational parameters; and last used operational parameters from a last time that the surgical tool was used.

Figure 6:
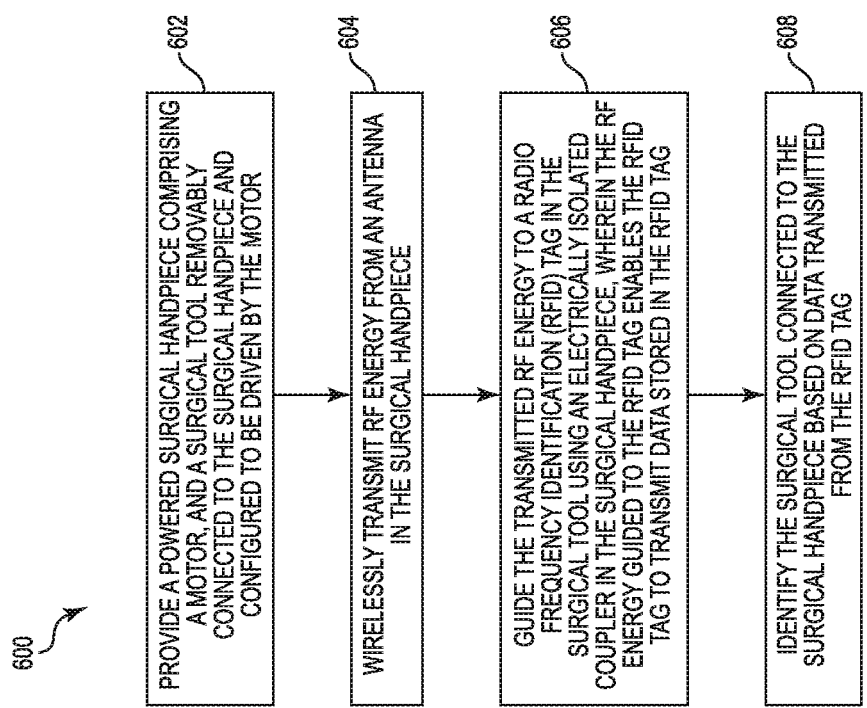
FIG. 6 is a flow diagram illustrating a method of identifying a surgical tool according to one embodiment.

Yet another embodiment is directed to a method of identifying a surgical tool. FIG. 6 is a flow diagram illustrating a method 600 of identifying a surgical tool according to one embodiment. In one embodiment, system 22 (FIG. 1) is configured to perform method 600. At 602 in method 600, a powered surgical handpiece comprising a motor, and a surgical tool removably connected to the surgical handpiece and configured to be driven by the motor are provided. At 604, RF energy is wirelessly transmitted from an antenna in the surgical handpiece. At 606, the transmitted RF energy is guided to a radio frequency identification (RFID) tag in the surgical tool using an electrically isolated coupler in the surgical handpiece, wherein the RF energy guided to the RFID tag enables the RFID tag to transmit data stored in the RFID tag. At 608, the surgical tool connected to the surgical handpiece is identified based on data transmitted from the RFID tag.

Embodiments disclosed herein provide numerous advantages over prior techniques. Embodiments disclosed herein allow utilization of the EPC Generation 2 ISO standard RFID tags. Operational guidance can be programmed into the RFID tag 214 rather than just a product ID. Some prior devices use spiral inductive coils and high frequency (HF—e.g., 13.56 MHz) or low frequency (LF—e.g., 134 KHz) based RFID techniques. In contrast, some embodiments disclosed herein use ultra-high frequency (UHF—e.g., 915 MHz), and do not use spiral inductive coils in the handpiece to excite the passive RFID tag 214. At UHF frequencies, such coils can become self-resonating with unpredictable behavior. Additionally, wire coils present challenges with manufacturing requiring the coils to be measured and tuned for performance. Additionally, the coils exhibit tuning instability when repeatedly exposed to high heat such as with autoclave sterilization.

The coupler 210 is a plastic encapsulated structure requiring no tuning or complicated installation. The coupler 210 is simple to manufacture, using, for example, a computer numerical control (CNC) fabrication process or metal stamping. The coupler 210 allows a simpler installation of the antenna 206 in the handpiece 20, and eliminates the need for a coaxial cable in the handpiece 20. No soldering to the coupler 210 is needed. The coupler 210 allows the antenna 206 to be designed into the back of the handpiece 20 or where ever is most optimal and not just near to where the RFID tag 214 is positioned. The coupler 210 is also tolerant and robust to manufacturing variations, autoclave sterilization cycles, and normal usage.

Embodiments disclosed herein perform blade recognition in powered surgical instruments, which is an important feature for the next generation of high speed burrs and blades. Different surgical tools 30 for handpiece 20 have parameters for optimal performance in terms of RPM, irrigation, rotational direction and oscillation speed. Blade recognition allows for operation guidance to be implemented on a per product basis, which improves safety and reduces risks.

Although the present disclosure has been described with reference to preferred embodiments, workers skilled in the art will recognize that changes can be made in form and detail without departing from the spirit and scope of the present disclosure.

What is claimed is:

1. A surgical system comprising:
a powered surgical handpiece comprising a motor;
wherein the surgical handpiece includes an antenna for wirelessly transmitting RF energy, and a coupler that is electrically isolated from the antenna and the UHF RFID tag and that is configured to guide the transmitted RF energy to the UHF RFID tag;
a surgical tool removably connected to the surgical handpiece and configured to be driven by the motor, wherein the surgical tool includes an ultra-high frequency (UHF) radio frequency identification (RFID) tag; and
a controller connected to the surgical handpiece and programmed to interface with the surgical handpiece, the controller including a data entry device and a display screen, wherein the controller is configured to identify the surgical tool connected to the surgical handpiece based on data stored in the UHF RFID tag.

2. The surgical system of claim 1, wherein the coupler is a passive metal structure encapsulated in plastic.

3. The surgical system of claim 1, wherein the surgical handpiece includes an RFID reader circuit that is configured to drive the antenna and read data from and write data to the UHF RFID tag.

4. The surgical system of claim 1, wherein the controller includes an RFID reader circuit that is configured to drive the antenna and read data from and write data to the UHF RFID tag.

5. The surgical system of claim 4, wherein the controller is coupled to the surgical handpiece via a cable that includes a twisted pair configured to deliver UHF RF energy to the antenna.

6. The surgical system of claim 1, wherein the UHF RFID tag stores authentication data including a unique serial number.

7. The surgical system of claim 1, wherein the UHF RFID tag stores parameter guidance data including operational limits and default operational parameters.

8. The surgical system of claim 1, wherein the UHF RFID tag stores last used operational parameters from a last time that the surgical tool was used.

9. A method of identifying a surgical tool, comprising:
providing a powered surgical handpiece comprising a motor, and a surgical tool removably connected to the surgical handpiece and configured to be driven by the motor;
wirelessly transmitting RF energy from an antenna in the surgical handpiece;
guiding the transmitted RF energy to a radio frequency identification (RFID) tag in the surgical tool using an electrically isolated coupler in the surgical handpiece, wherein the RF energy guided to the RFID tag enables the RFID tag to transmit data stored in the RFID tag; and
identifying the surgical tool connected to the surgical handpiece based on data transmitted from the RFID tag.

* * * * *